United States Patent
Nam

(10) Patent No.: US 7,244,305 B1
(45) Date of Patent: Jul. 17, 2007

(54) ANTIBACTERIAL GYPSUM COMPOSITION FOR DENTAL SURGERY

(76) Inventor: Doo Suek Nam, 101-1025, Jawoo Apts., 740, Goejeong-dong, Saha-gu, Busan, 604-764 (KR)

( * ) Notice: Subject to any disclaimer, the term of this patent is extended or adjusted under 35 U.S.C. 154(b) by 0 days.

(21) Appl. No.: 11/479,653

(22) Filed: Jun. 30, 2006

(30) Foreign Application Priority Data

Jun. 15, 2006 (KR) .................. 10-2006-0053969

(51) Int. Cl.
*C04B 24/12* (2006.01)
*C04B 11/00* (2006.01)
*C04B 103/67* (2006.01)
*A61K 6/06* (2006.01)
*A01N 57/00* (2006.01)

(52) U.S. Cl. ................. 106/781; 106/18.32; 106/35; 514/114; 514/115

(58) Field of Classification Search ............. 106/18.32, 106/35, 781; 514/114, 115
See application file for complete search history.

(56) References Cited

U.S. PATENT DOCUMENTS

| | | | | |
|---|---|---|---|---|
| 4,196,008 A | * | 4/1980 | Kennedy-Skipton | ........ 106/694 |
| 5,746,822 A | * | 5/1998 | Espinoza et al. | ........... 106/785 |
| 6,740,395 B2 | * | 5/2004 | Halm et al. | .............. 428/292.4 |
| 6,805,741 B1 | * | 10/2004 | Liu et al. | .................... 106/785 |

FOREIGN PATENT DOCUMENTS

| | | |
|---|---|---|
| KR | 1019880001750 B1 | 9/1988 |
| KR | 100219421 B1 | 6/1999 |
| KR | 100392609 B1 | 7/2003 |
| KR | 1020030060440 A | 7/2003 |
| KR | 102004003492 A | 4/2004 |
| KR | 1020040090677 A | 10/2004 |

* cited by examiner

*Primary Examiner*—Anthony J. Green
(74) *Attorney, Agent, or Firm*—Renner, Otto, Boisselle & Sklar, LLP

(57) ABSTRACT

Disclosed is an antibacterial gypsum composition for dental surgery, which eliminates pathogens transferred from the mouth of a patient, so that a dentist or others participating in dental surgery can be prevented from being infected by such pathogens during the work for dental surgery. The antibacterial gypsum composition for dental surgery comprises α-plaster for a dental model and an organic nitrogen-based compound, polyhexamethylene guanidine phosphate, as an antibacterial agent.

3 Claims, No Drawings

ANTIBACTERIAL GYPSUM COMPOSITION FOR DENTAL SURGERY

BACKGROUND OF THE INVENTION

1. Field of the Invention

The present invention relates to an antibacterial gypsum composition for dental surgery. More particularly, the present invention relates to an antibacterial gypsum composition for dental surgery, which eliminates pathogens transferred from the mouth of a patient, so that a dentist or others participating in dental surgery can be prevented from being infected by such pathogens during work for dental surgery.

2. Description of the Prior Art

In general, calcined gypsum is hydraulic gypsum (which is curable upon the reaction with water), and thus is used as a material for making a model in various applications.

Particularly, calcined gypsum is essential to make a denture model for producing various dentures, including a total denture, a partial denture, a crown, a bridge, an inlay and an occlusion frame, mounted in the oral cavity.

In general, a denture model is obtained by the method comprising the steps of: forming a negative mold, also referred to as an impression, by using an impressing material; and pouring calcined gypsum slurry dissolved in water into the negative mold; and setting the model.

Conventional impressing materials include rubber (e.g. silicone rubber, polyether rubber and polysulfide rubber) and hydrocolloid (e.g. agar and alginate).

Materials used for a denture model are required to have a sufficient dimension precision, mechanical strength, soft surface-forming capability upon the contact with various impressing materials, easy handling property, stability with a lapse of time and processability. Also, such materials should not cause a significant foaming phenomenon.

To improve a dimension precision, JP-A 50-161492 (herein, JP-A refers to "Japanese unexamined laid-open patent application) discloses a method of inhibiting gypsum from expanding upon the setting by adding an anti-expanding agent such as a sulfate, tartrate or oxalate.

To obtain a gypsum model having a high strength, a high hardness and a soft surface, it is known that a metal sulfate and melamine-formaldehyde resin is added to a type calcined gypsum (see JP-A 62-270451).

Hydrocolloid impressing materials such as agar and alginate have a disadvantage in that a gypsum model molded from such hydrocolloid materials cannot represent a soft surface. However, a composite material formed of agar and alginate, which has been developed recently, provides the advantages of agar as well as the easy handling property and cost efficiency of alginate, and thus are widely used for clinical applications.

However, the aforementioned gypsum compositions have no antibacterial or sterilizing function. Thus, when a tooth model is formed in the oral cavity of a dental patient by using gypsum, various pathogens present in the oral cavity may be attached to the gypsum and transferred to the exterior. As a result, dental technicians fabricating gypsum models or dentists handling gypsum models may be infected with such pathogens.

SUMMARY OF THE INVENTION

Accordingly, the present invention has been made to solve the above-mentioned problems occurring in the prior art. An object of the present invention is to provide an antibacterial gypsum composition for dental surgery, which can prevent secondary infection of pathogens.

Another object of the present invention is to provide an antibacterial gypsum composition for dental surgery, which can destroy pathogens present in the oral cavity of a patient.

In order to accomplish this object, there is provided an antibacterial gypsum composition for dental surgery, which comprises α-plaster for a dental modal and an organic nitrogen-based compound as an antibacterial agent.

Preferably, the antibacterial agent is polyhexamethylene guanidine phosphate.

More particularly, the α-plaster comprises 38.0 wt % of CaO, 54.5 wt % of $SO_3$, 6.20 wt % of combined water, 0.7 wt % of $(CH_2COOH)_2$, and 0.60 wt % of $K_2SO_4$.

The α-plaster and the antibacterial agent are mixed in a ratio of 1000:1.

DETAILED DESCRIPTION OF THE PREFERRED EMBODIMENTS

Hereinafter, the antibacterial gypsum composition for dental surgery according to the present invention will be explained in more detail.

The gypsum composition according to the present invention is characterized in that it shows an antibacterial effect by adding an antibacterial agent, which is not harmful to the human body, does not cause skin irritation and is suitable for a hygienic processing aid, to dental gypsum used as a material for making a dental model.

The gypsum composition according to the present invention comprises α-plaster and an organic nitrogen-based compound, polyhexamethylene guanidine phosphate, as the antibacterial agent. Herein, the α-plaster and the antibacterial agent are mixed preferably in a ratio of 1000:1.

The α-plaster comprises 38.0 wt % of CaO, 54.5 wt % of $SO_3$, 6.20 wt % of combined water, 0.7 wt % of $(CH_2COOH)_2$, and 0.60 wt % of $K_2SO_4$.

Polyhexamethylene guanidine phosphate is very safe antibacterial agent having an antibacterial effect to a broad spectrum of bacteria. Also, polyhexamethylene guanidine phosphate does not cause skin irritation, and thus is suitable for a hygienic processing agent and other applications.

Additionally, polyhexamethylene guanidine phosphate is present in the form of white powder with pH 6.5~7, and is effective against various kinds of bacteria.

Polyhexamethylene guanidine phosphate is represented by the following formula:

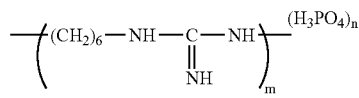

wherein m/n=1~2.

The gypsum composition according to the present invention is obtained by the method as described hereinafter.

(1) Natural gypsum is pulverized.

Natural ore is pulverized crudely into a size of an apricot (diameter: 30~50 mm), and then finely divided into a size of sugar (diameter: 0.3~0.5 mm).

(2) The finely divided material is subjected to a process of producing α-plaster, followed by drying at a temperature of 180° C. for 2~3 hours.

The dried material is introduced into a furnace and baked in the furnace under pressure at a temperature of about 700~800° C. for about 2.5 hours.

(3) The α-plaster obtained from the preceding step is further finely divided by passing it through a sieve and an electromagnet into micropowder like wheat flour (diameter: 50 μm).

(4) Adding polyhexamethylene guanidine phosphate, as an antibacterial agent, to the α-plaster obtained from the preceding step to provide an antibacterial gypsum composition. Preferably, the α-plaster and the antibacterial agent are mixed in a ratio of about 1000:1.

EXAMPLE

The antibacterial gypsum composition for dental surgery, obtained by the above-described method, was used as a sample and subjected to an antibacterial test. Hereinafter, the antibacterial test and the results thereof will be described.

<Test Sample>

A clod of gypsum obtained by adding polyhexamethylene guanidine phosphate, as an antibacterial agent, to gypsum powder and solidifying the resultant mixture, was used as a sample.

<Test>: SHAKING FLASK TEST (Shaking flask method defined by SIAA standards>

(1) Strain

*Escherichia coli* (ATCC No. 8739)

*Staphylococcus aureus* (ATCC No. 6538p)

(2) Culture medium

Buffer: buffer solution with pH 6.8

Nutrient agar medium (available from Difco): 0.3% of glucose added.

(3) Culture temperature and period after inoculation of the strain cultured in a shaking incubator at 30° C. for 24 hours.

(4) Test method

The sample (10 g) was cut and introduced into phosphate buffered saline containing the bacterial strain diluted to a predetermined concentration (about $10^4$~$10^5$), and then was cultured in a shaking incubator set at a temperature of 30° C. for 24 hours. The cultured solution was collected at the initial time and 24 hours after the culture. Then, viable cells were counted and antibacterial effect was determined.

<Results>

TABLE 1

| Sample | *Eschreichia coli* (ATCC NO. 8739) (CFU/ml) | | | *Staphylococcus aureus* (ATCC (NO. 6538p) (CFU/ml) | | |
|---|---|---|---|---|---|---|
| | Initial cell count | Cell count after 24 hours | Antibacterial effect (%) | Initial cell count | Cell count after 24 hours | Antibacterial effect (%) |
| Comp. Ex. (no antibacterial agent) | 2.9 × $10^4$ | 1.6 × $10^7$ | — | 1.1 × $10^4$ | 6.4 × $10^4$ | |
| Present invention (containing antibacterial agent) | | <10 | 99.9 | | 10 | 99.9 |

As shown in Table 1, in the gypsum composition containing no antibacterial agent, many viable cells were present after 24 hours. On the contrary, in the composition containing the antibacterial agent according to the present invention, merely 10 or less viable cells were present after 24 hours. In other words, the gypsum composition according to the present invention shows an antibacterial effect of about 99.9%.

Therefore, the antibacterial gypsum composition according to the present invention can destroy pathogens, and thus can prevent secondary infection.

As can be seen from the foregoing, the antibacterial gypsum composition for dental surgery according to the present invention destroys pathogens by itself, and thus can prevent a dentist or a dental technician from being secondarily infected with the pathogens.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. An antibacterial gypsum composition for dental surgery, which comprises an α-plaster for a dental model and an organic nitrogen-based compound as an antibacterial agent, the antibacterial agent being polyhexamethylene guanidine phosphate, represented by the following formula:

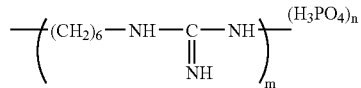

wherein m/n=1~2.

2. The antibacterial gypsum composition for dental surgery as claimed in claim 1, wherein the α-plaster comprises 38.0 wt % of CaO, 54.5 wt % of $SO_3$, 6.20 wt % of combined water, 0.7 wt % of $(CH_2COOH)_2$, and 0.60 wt % of $K_2SO_4$.

3. The antibacterial gypsum composition for dental surgery as claimed in claim 1, wherein the α-plaster and the antibacterial agent are mixed in a ratio of 1000:1.

* * * * *